United States Patent [19]

Mack

[11] Patent Number: 4,459,108
[45] Date of Patent: Jul. 10, 1984

[54] ACCESSORY DEVICE FOR A DENTAL ARTICULATOR FOR THREE-DIMENSIONAL DETERMINATION OF THE DIFFERENCES

[76] Inventor: Heinz Mack, Südl. Auffahrtsallee 64, 8000 München 19, Fed. Rep. of Germany

[21] Appl. No.: 455,515

[22] Filed: Jan. 4, 1983

[30] Foreign Application Priority Data

Jan. 14, 1982 [DE] Fed. Rep. of Germany ....... 3200890

[51] Int. Cl.³ ............................................. A61C 11/00
[52] U.S. Cl. ..................................................... 433/55
[58] Field of Search ........................ 433/55, 56, 59, 57, 433/58, 73

[56] References Cited

U.S. PATENT DOCUMENTS

| | | | |
|---|---|---|---|
| 1,622,910 | 3/1927 | Homer | 433/57 |
| 3,048,923 | 8/1962 | Franwick | 433/55 |
| 3,896,550 | 7/1975 | Lee | 433/57 |

*Primary Examiner*—Robert Peshock
*Attorney, Agent, or Firm*—Larson and Taylor

[57] ABSTRACT

The present invention relates to an accessory device for a dental articulator by means of which the differences of the joint positions between central occlusion (intercuspidal occlusion position) and central relation (retral contact position) can be measured in all three dimensions. The accessory device consists of an upper frame portion for a dental articulator which, in lieu of the ball sockets, has measuring means mounted on the bearing shafts 12 so as to be laterally shiftable, said measuring means 60 having a ball contacting face 61 provided with a measuring label for determining the deviations on the x and z axes, and each bearing shaft 12 having an axial point 62 capable of extending through a bore 63 in the ball contacting face 61 in order to mark the central relation on the adhered measuring label by perforation thereof, said measuring means additionally having a distance measuring surface 64 disposed parallel to the ball contacting face 61 for measurement of the transversal shift on the y axis.

5 Claims, 4 Drawing Figures

ACCESSORY DEVICE FOR A DENTAL ARTICULATOR FOR THREE-DIMENSIONAL DETERMINATION OF THE DIFFERENCES

DESCRIPTION

The present invention relates to an accessory device for a dental articulator by means of which the difference of the joint positions between central occlusion (intercuspidal occlusion position) and central relation (retral contact position) can be measured in all three dimensions.

From mathematical-geometrical studies it has become known that relatively small shifting distances within the occulusion must result in larger shifting distances in the joint surfaces positioned farther remote.

The dental articulator per se as described, for example, in U.S. Pat. No. 4,058,895, is not capable of precisely indicating these shifts because the ball sockets serving as fossae form a cage guiding the ball elements. However, this also eliminates the three-dimensional freedom required for discerning the reactions of the occlusal motions of the joint. On account of the ball sockets and the balls the upper portion and the lower portion of the articulator are disposed in a predetermined relation to each other. It is only without said ball sockets that the interrelations between the teeth alone determine the relation of the upper portion to the lower portion of the articulator. This follows from the contact between the jaw models and from the comparison with various registrats.

Therefore, it is the object of the present invention to replace the conventional upper frame portion of the dental articulator provided with ball sockets, after the measurements carried out with said portion, by a virtually identical upper frame portion which, in lieu of the ball sockets, has means permitting three-dimensional determination of the differences of the joint positions between central occlusion (intercuspidal occlusion position) and central relation (retral contact position).

This problem is solved in that, instead of the ball sockets mounted on the bearing shafts the upper frame portion has measuring means mounted on the bearing shafts so as to be laterally slidable from the inside outwardly up to the balls but non-rotative relative to said shafts, said measuring means each having a ball contacting face extending perpendicular to the cross section of the bearing shaft and tangentially contacting the ball and provided with a measuring label, and each bearing shaft has an axial point capable of extending through a bore in the ball contacting face to mark on the measuring label the central relation corresponding to the course of the articulator axis by perforation of the measuring label, said measuring means each having a distance measuring surface disposed parallel to the ball contacting face permitting the measurement of the transversal shift, i.e. the distance of the ball contacting face from the marginal surface of the base of the upper frame portion.

The fact that the measuring means are shifted from the inside outwardly to contact the balls, i.e. that the measurement is performed between the balls, offers the significant advantage of excluding reciprocal or distorted indication. Moreover, the tangential contact of the ball contacting face on the ball already furnishes a two-dimensional indication of the x and z axes.

Lateral shifting, also referred to as transversal or axial shifting, on the y axis is determined by measurement of the change in the distance of the ball contacting face from the normal position. To this end known calipers such as dial gauges, a vernier sliding gauge on the bearing shaft, or a wedge gauge pushed between the vertically downwardly extending surfaces of the base of the upper frame portion and the distance measuring surface of the measuring means may be employed. For this purpose the marginal faces of the base of the upper frame portion into which the bearing shafts extend preferably extend perpendicular with respect to the cross section of the bearing shaft and thus also parallel to the distance measuring surface of the measuring means which, in turn, extends parallel to the ball contacting face of the measuring means.

In case a dial gauge is employed it is disposed either on the upper side of the upper frame portion above the bearing shafts, or preferably at the end face of the base of the upper frame portion into which the bearing shafts extend. The dial gauge is a known spring-loaded indicating means.

Of course, transversal shifting of the measuring means could be effected also by means of other known optical, acoustical or electronic means as far as this is acceptable from an economical point of view.

The measuring means itself may have any desired configuration, e.g. it may be a cube, a block, a cylinder, a barrel or a plate with a tubular projection into which the bearing shaft extends. However, preferably it is cube-shaped.

The non-rotative mounting of the measuring means on the respective bearing shaft may be effected, for example, by way of a suitable longitudinal profile of the bearing shaft. With at least one groove in each measuring means extending in the direction of the bearing shaft and having stops on both sides for slidingly receiving a guide pin fixed to and extending transversely from the bearing shaft an especially simple non-rotative arrangement can be realized with little constructional investment.

Further details and features of the invention will become apparent from the following description in conjunction with the attached drawings. The drawings with reference to which the invention will be further explained only illustrate preferred embodiments of the accessory device of the invention. Therefore, the invention itself is not to be limited to these preferred embodiments. The reference numerals contained in the description and the figures are compiled at the end of the description in the "List of Reference Numerals".

Figure 1:
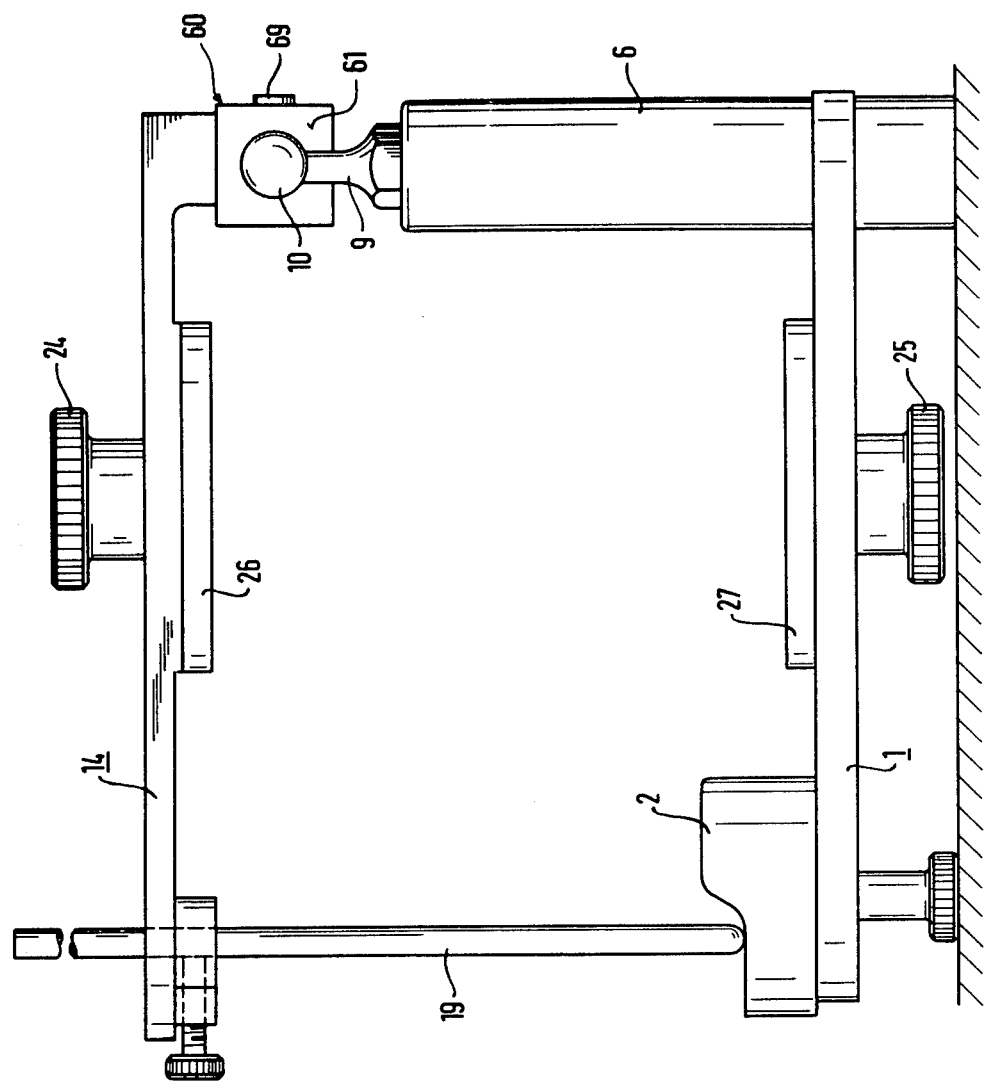
FIG. 1 is a lateral view of the accessory device of the invention which is installed in a dental articulator (the jaw models are not shown)
Figure 2:
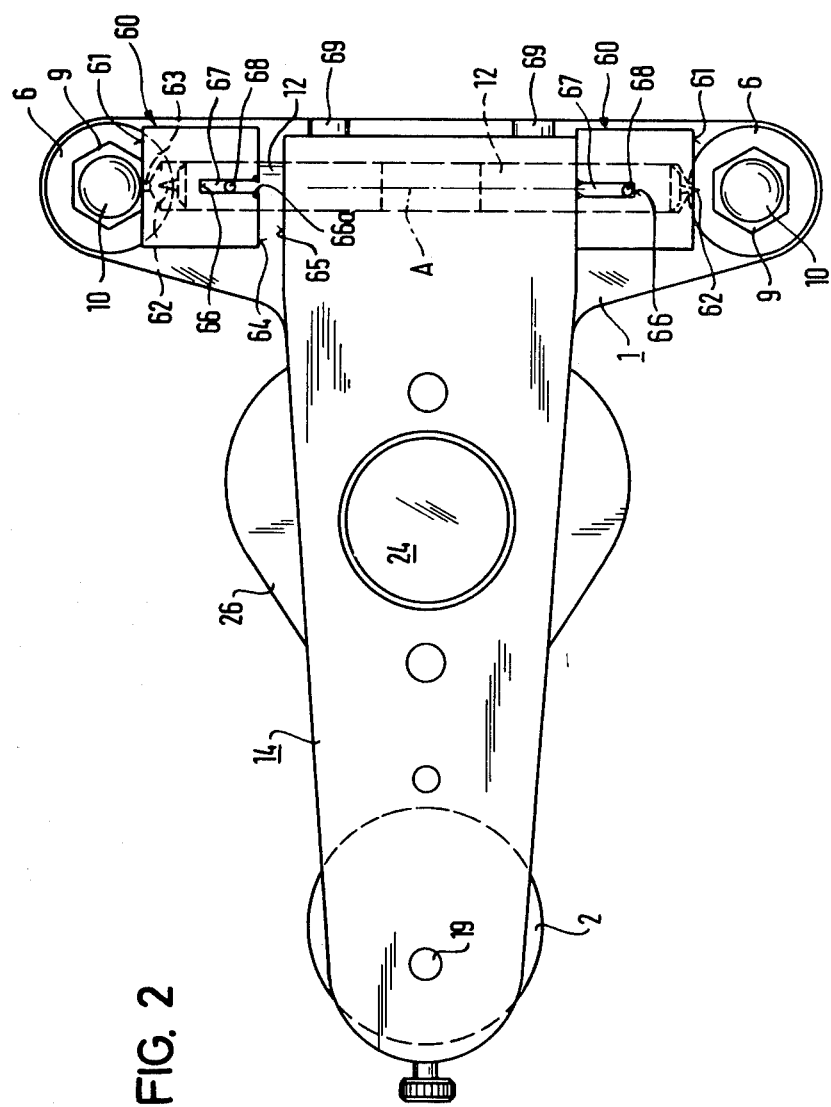
FIG. 2 is a plan view of the illustration of FIG. 1.
Figure 3:
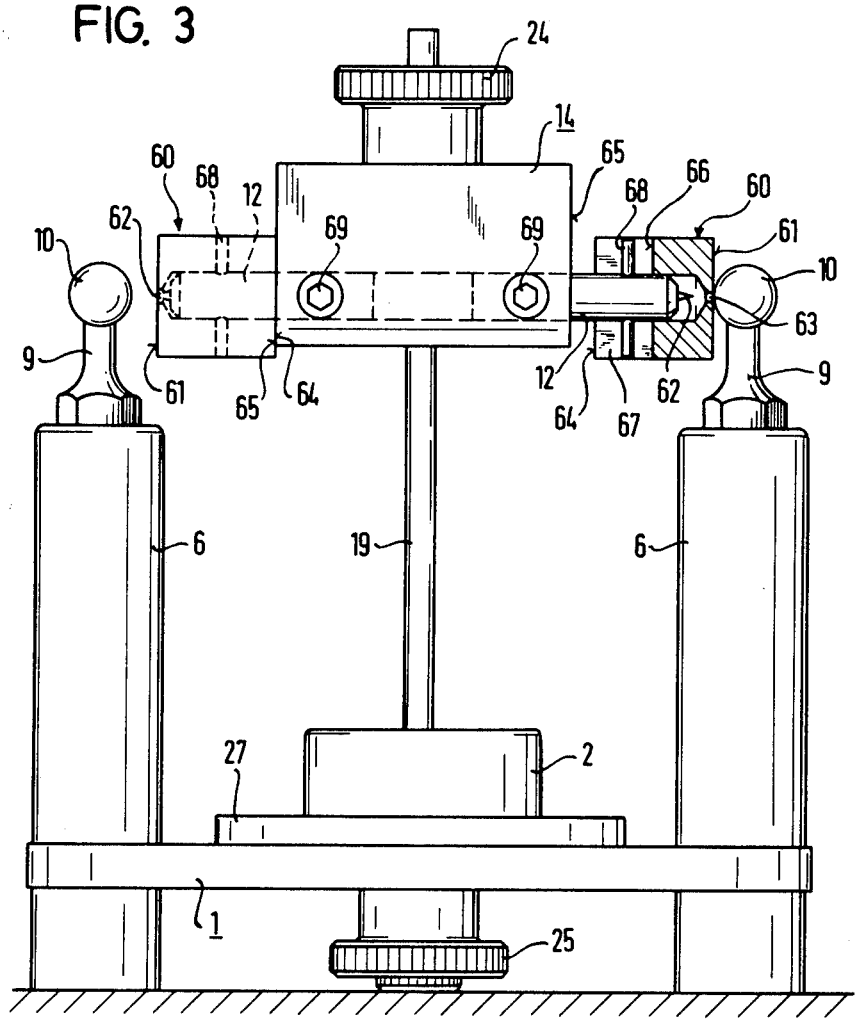
FIG. 3 is a rear view of the apparatus shown in FIG. 1.
Figure 4:
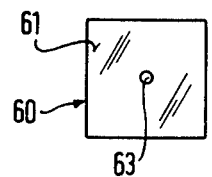
FIG. 4 shows the ball contacting face of a measuring means.

For simplicity's sake both the lower jaw model and the upper jaw model were omitted in the illustrations of FIGS. 1 to 3. The lower portion of the dental articulator provided with the device of the invention consists of a lower frame portion 1 with a screw 25 for fastening the lower jaw model provided with mounting plate. On the lower frame portion 1 a supporting platform 2 is mounted on which the incisor guide pin 19 rests. On the side opposite the supporting platform 2 the lower frame portion 1 widens on both sides to form regions for receiving the supporting pillars 6 supporting with their lower ends the lower frame portion 1 and extending vertically upwardly to the supporting stems 9. The supporting stems 9, at their upper ends, terminate in the balls 10 serving as condyles.

In parallel to the lower frame portion 1 there is the upper frame portion 14 having a screw 24 for fastening the upper jaw model provided with the mounting plate. The incisor guide pin 19 is mounted in the upper frame portion 14 at the front end thereof. On the side opposite said incisor guide pin 19 cube-shaped measuring means 60 are arranged in the region of the balls 10, each with a ball contacting face 61 facing the respective balls 10 and mounted non-rotatively on a bearing shaft 12. The bearing shafts 12, in turn, are mounted in a matching bore through the upper frame portion 14 by means of the fastening screws 69.

The bearing shafts 12 end in an axial point 62 contemplated for passing through a bore 63 ending in the ball contacting face 61 when the measuring means 60 bears against the upper frame portion 14. In this way the position of the articulator axis A, with which the bearing shafts 12 are in register in the central relation of the teeth, can be readily marked on the measuring label by means of point-shaped perforation. The measuring label, not shown in the figures, may preferably have an adhesive coating on the back side for adhesion to the ball contacting faces 61 and may be pressure-sensitive, or an inked film is placed in-between. In this way a suitable data registration may be effected solely by the dot-shaped contact pressure.

On the side facing away from the ball contacting face 61 each measuring means 60 has a distance measuring surface 64 extending perpendicular to the cross section of the bearing shaft 12 with which the measuring means 60 may be shifted to contact the marginal face 65 of the upper frame portion 14. Each measuring means 60 is slidable non-rotatively in that at least one groove 67 provided with stops 66 on both sides and extending in the direction of the longitudinal axis of the bearing shaft 12 is adapted to slidingly receive a guide pin 68 fixed to and extending transversely from the bearing shaft 12, as apparent from FIG. 2. The stop 66a for the guide pin 68 is formed in the region of the open groove by minor deformation of the groove opening.

In the manner illustrated in the drawing the apparatus of the invention permits three-dimensional determination of the differences of the joint positions between central occlusion (intercuspidal occlusion position) and central relation (retral contact position) easily and simply realizable with little apparative investment.

For three-dimensional determination of the differences of the joint positions one proceeds as follows: The hitherto used upper articulator frame portion is exchanged for the accessory device of the invention with the measuring means 60 provided thereon; suitable adhesive labels are provided at the ball contacting faces 61 of the measuring means 60. The models are moved into intercuspidal occlusion position. In case this position is not unequivocal, it may be found by way of habitual biting recordal. In this position of the models the measuring means 60 are shifted outwardly up to tangential contact with the balls 10. If no pressuresensitive measuring label is used, the position may also be marked by means of an inked film placed over the measuring labels.

The marking on the measuring label corresponds to the displacement of the ball (condyle) by the occlusal constrained position. Transversal shifting may be determined very simple by a wedge gauge measuring the deviation from the standard distance between the distance measuring surface 64 of the measuring means 60 and the marginal area 65 of the base of the upper frame portion 14. The centric relation is automatically marked on the adhesive labels at the measuring means 60 in that the provided axial points 62 of the bearing shafts 12 perforate, as articulator axis, the respective measuring label when the measuring means 60 is shifted back along the upper frame portion. Hence, reference marking with the centric registrat is superfluous, because the articulator axis represents the centric mounting.

LIST OF REFERENCE NUMERALS 1 lower frame portion
2 supporting platform
6 supporting pillars
9 supporting stems
10 balls
12 bearing shafts
14 upper frame portion
19 incisor guide pin
24 screws for fastening mounting plate 26
25 screws for fastening mounting plate 27
26 mounting plate
27 mounting plate
60 measuring means
61 ball contacting face of mounting means 60
62 axial point of bearing shafts 12
63 bore in ball contacting faces 61
64 distance measuring surface of measuring means 60
65 marginal surface of base of upper frame portion
66 stop
66a stop
67 groove
68 guide pins at the bearing shafts 12
69 mountings for the bearing shafts 12

I claim:

1. A device for three-dimensional determination of the difference of the joint positions between central occlusion and central relation, comprising, a lower frame portion with means for securing a mounting plate for the lower jaw model and a supporting platform for an incisor guide pin, a vertical frame portion rigidly connected to the lower frame portion and having two balls serving as condyles which are mounted on two supporting stems, an upper frame portion having bearing shafts, means for supporting the mounting plate of the upper jaw model, and an adjustable incisor guide pin, said bearing shafts having measuring means mounted thereon and being slidable laterally outwardly to the balls but non-rotative relative to said bearing shafts, said measuring means each having a ball contacting face extending perpendicular to the axis of the bearing shafts and tangentially contacting the ball and provided with a measuring label, and each bearing shaft having an axial point capable of extending through a bore in the ball contacting face in order to mark on the measuring label the central relation corresponding to the course of the articulator axis by perforation of the measuring label, said measuring means each having a distance measuring surface disposed parallel to the ball contacting face to permit measurement of the distance of the ball contacting face from the marginal surface of the base of the upper frame portion.

2. Apparatus according to claim 1 characterized in that the marginal surface of the base of the upper frame portion likewise extends perpendicular to the axis of the bearing shaft and thus also parallel to the ball contacting face.

3. Apparatus according to claim 1 characterized in that each measuring means has at least one groove extending in the direction of the axis of the bearing shaft and provided with a stop, said groove slidingly receiving a guide pin fixed to and extending transversely with respect to the axis of the bearing shaft.

4. Apparatus according to claim 1 characterized in that each measuring means has the shape of a cube.

5. Apparatus according to claim 1 characterized in that at the upper frame portion the measuring means is rotatably mounted for determining the transversal shift with an indicator bearing against the distance measuring surface.

* * * * *